United States Patent
Liao et al.

(10) Patent No.: US 10,605,786 B2
(45) Date of Patent: Mar. 31, 2020

(54) ULTRASONIC WAVE SENSING DEVICE

(71) Applicants: Interface Technology (ChengDu) Co., Ltd., Sichuan (CN); Interface Optoelectronics (ShenZhen) Co., Ltd., Guangdong (CN); General Interface Solution Limited, Miaoli County (TW)

(72) Inventors: Chih-Lin Liao, Guangdong (CN); I-Chang Kuan, Guangdong (CN)

(73) Assignees: INTERFACE TECHNOLOGY (CHENGDU) CO., LTD., Sichuan (CN); INTERFACE OPTOELECTRONICS (SHENZHEN) CO., LTD., Guangdong (CN); GENERAL INTERFACE SOLUTION LIMITED, Miaoli County (TW)

( * ) Notice: Subject to any disclaimer, the term of this patent is extended or adjusted under 35 U.S.C. 154(b) by 124 days.

(21) Appl. No.: 15/919,180

(22) Filed: Mar. 12, 2018

(65) Prior Publication Data
US 2019/0242856 A1   Aug. 8, 2019

(30) Foreign Application Priority Data
Feb. 8, 2018   (CN) .......................... 2018 1 0129953

(51) Int. Cl.
*G01N 29/24* (2006.01)
*G06F 3/043* (2006.01)
*G01H 11/08* (2006.01)

(52) U.S. Cl.
CPC ............. *G01N 29/24* (2013.01); *G01H 11/08* (2013.01); *G06F 3/043* (2013.01)

(58) Field of Classification Search
CPC ...... G01H 11/08; G06K 9/0002; G01N 29/24; G06F 3/043
USPC ......... 73/610, 611; 367/97; 310/316.01, 319
See application file for complete search history.

(56) References Cited

U.S. PATENT DOCUMENTS 9,607,203 B1 * 3/2017 Yazdandoost ........ A61B 5/1172
2019/0079186 A1 * 3/2019 Taghibakhsh ......... B06B 1/0622

* cited by examiner

*Primary Examiner* — David Z Huang
(74) *Attorney, Agent, or Firm* — CKC & Partners Co., LLC

(57) ABSTRACT

Ultrasonic wave sensing device includes a reading transistor, an ultrasonic wave transducer, and an input circuit. The reading transistor includes a first node, a second node, and a control node, wherein the first node receives a reference voltage, the second node couples with a reading node, and the control node couples with a first signal node. The ultrasonic wave transducer couples between the first signal node and a first input node, and receives a first control signal from the first input node. The input circuit couples between the first signal node and a second input node, and receives a second control signal from the second input node. The ultrasonic wave transducer generates an ultrasonic wave according to the first control signal and the second control signal, and outputs a sensing signal to the control node according to a reflected sound wave.

8 Claims, 4 Drawing Sheets

ULTRASONIC WAVE SENSING DEVICE

CROSS-REFERENCE TO RELATED APPLICATION

This application claims priority to Chinese Application Serial Number 201810129953.6, filed Feb. 8, 2018, which is herein incorporated by reference in its entirety.

BACKGROUND

Field of Invention

The present disclosure relates to a sensing device. More particularly, the present disclosure relates to an ultrasonic wave sensing device.

Description of Related Art

The ultrasonic wave sensing system has advantages such as high resolution. When a user presses his/her finger on the interface of the ultrasonic wave sensing system, the ultrasonic wave sensing system may obtain the finger print by analyzing the received reflected sound waves of various intensities. However, the traditional ultrasonic wave sensing system often needs to include an individual ultrasonic wave emission layer and an individual ultrasonic wave receiving layer, wherein the ultrasonic wave emission layer and ultrasonic wave receiving layer are configured to be correspondingly located. The ultrasonic wave emission layer, for example, may be configured to be located upon or beneath the ultrasonic wave receiving layer. As a result, the traditional ultrasonic wave sensing system has a multi-layer structure, and thereby does not facilitate miniaturization of the whole system.

SUMMARY

The disclosure provides an ultrasonic wave sensing device. The ultrasonic wave sensing device comprises a reading transistor, an ultrasonic wave transducer, and an input circuit. The reading transistor comprises a first node, a second node, and a control node, wherein the first node of the reading transistor is configured to receive a reference voltage, the second node of the reading transistor is configured for coupling with a reading node, and the control node of the reading transistor couples with a first signal node. The ultrasonic wave transducer couples between the first signal node and a first input node, and is configured to receive a first control signal from the first input node. The input circuit couples between the first signal node and a second input node, and is configured to receive a second control signal from the second input node. The ultrasonic wave transducer is further configured to generate an ultrasonic wave according to the first control signal and the second control signal, and configured to output a sensing signal to the control node of the reading transistor according to a reflected sound wave corresponding to the ultrasonic wave.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
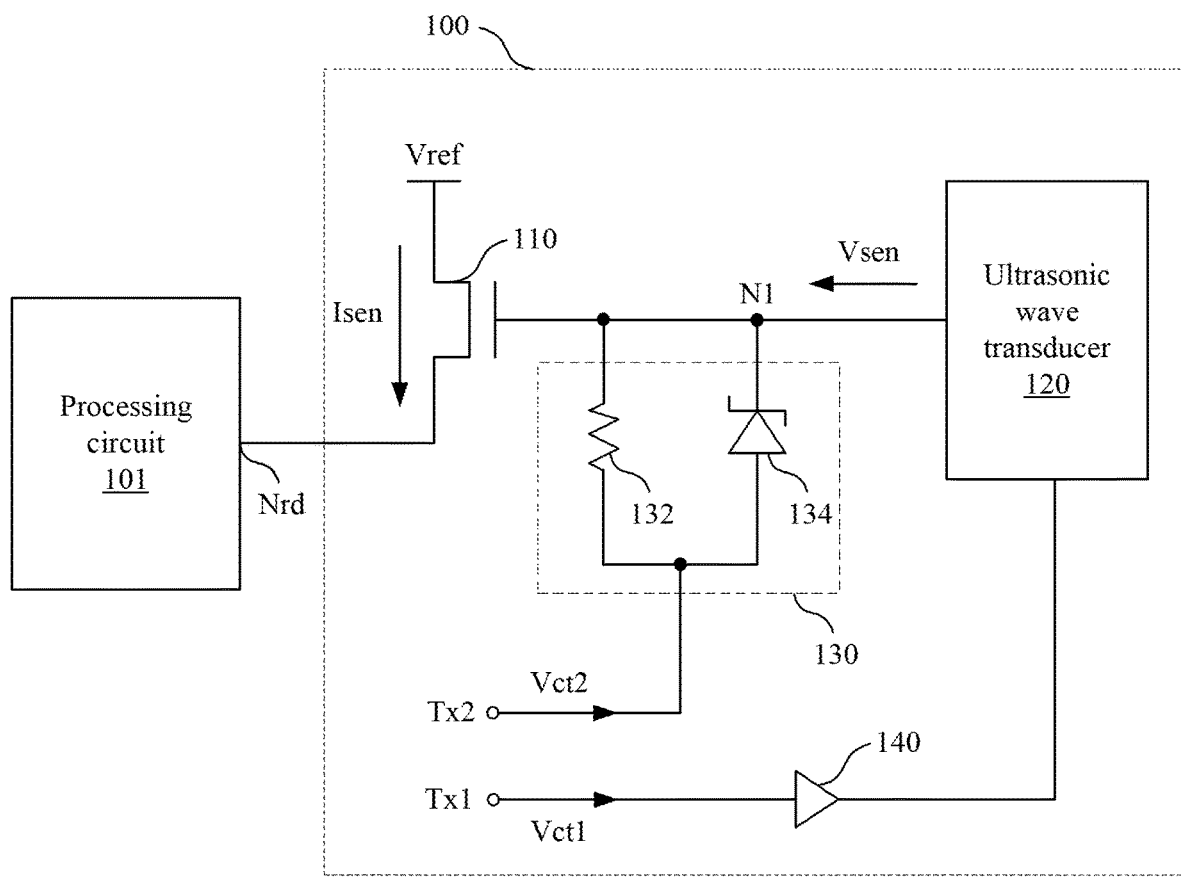
FIG. 1 is a simplified functional block diagram of an ultrasonic wave sensing device according to one embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

FIG. 1 is a simplified functional block diagram of an ultrasonic wave sensing device 100 according to one embodiment of the present disclosure. The ultrasonic wave sensing device 100 comprises a reading transistor 110, an ultrasonic wave transducer 120, an input circuit 130, and an amplifier 140. The ultrasonic wave sensing device 100 may generate an ultrasonic wave, and may receive a reflected sound wave corresponding to the ultrasonic wave. The ultrasonic wave sensing device 100 may further determine the magnitude of a sensing current Isen according to the received reflected sound wave, wherein the sensing current Isen is outputted by the ultrasonic wave sensing device 100 to the processing circuit 101. The processing circuit 101 may determine whether an object (not shown in FIG. 1) is nearby the ultrasonic wave sensing device 100 according to the sensing current Isen. For the sake of brevity, other functional blocks of the ultrasonic wave sensing device 100 are not shown in FIG. 1.

The first node of the reading transistor 110 is configured to receive the reference voltage Vref, the second node of the reading transistor 110 is configured for coupling with the reading node Nrd of the processing circuit 101, and the control node of the reading transistor 110 couples with the first signal node N1. The reading transistor 110 may determine the magnitude of the sensing current Isen according to the sensing signal Vsen received by the control node of the reading transistor 110. In addition, the sensing current Isen flows to the reading node Nrd of the processing circuit 101 through the reading transistor 110.

The ultrasonic wave transducer 120 couples between the first signal node N1 and the first input node Tx1, and is configured to receive a first control signal Vct1 from the first input node Tx1. The ultrasonic wave transducer 120 may generate the aforesaid ultrasonic wave according to the first control signal Vct1. On the other hand, when the ultrasonic wave transducer 120 receives the reflected sound wave corresponding to the ultrasonic wave, the ultrasonic wave transducer 120 may output a sensing signal Vsen to the first signal node N1 according to the received reflected sound wave.

The input circuit 130 couples between the first signal node N1 and the second input node Tx2, and is configured to receive a second control signal Vct2 from the second input node Tx2. The input circuit 130 may determine the voltage level of the first signal node N1 according to the second control signal Vct2, and may keep the voltage level of the first signal node N1 lower than a predetermined voltage to protect the reading transistor 110 from being damaged by over voltage.

In this embodiment, the input circuit 130 comprises a resistor 132 and a Zener diode 134. The resistor 132 couples between the first signal node N1 and the second input node Tx2. The cathode node of the Zener diode 134 couples with the first signal node N1, and the anode node of the Zener diode 134 couples with the second input node Tx2.

The amplifier 140 couples between the first input node Tx1 and the ultrasonic wave transducer 120 in a series connection, so as to amplify the first control signal Vct1.

In practice, the processing circuit 101 may be realized with the application-specific integrated circuit (ASIC), field-programmable gate array (FPGA), or any suitable microprocessor. The reading transistor 110 may be realized with any suitable n-type transistor. The ultrasonic wave transducer 120 may be realized with a multi-layer structure containing any type of suitable piezoelectric material.

Figure 2:
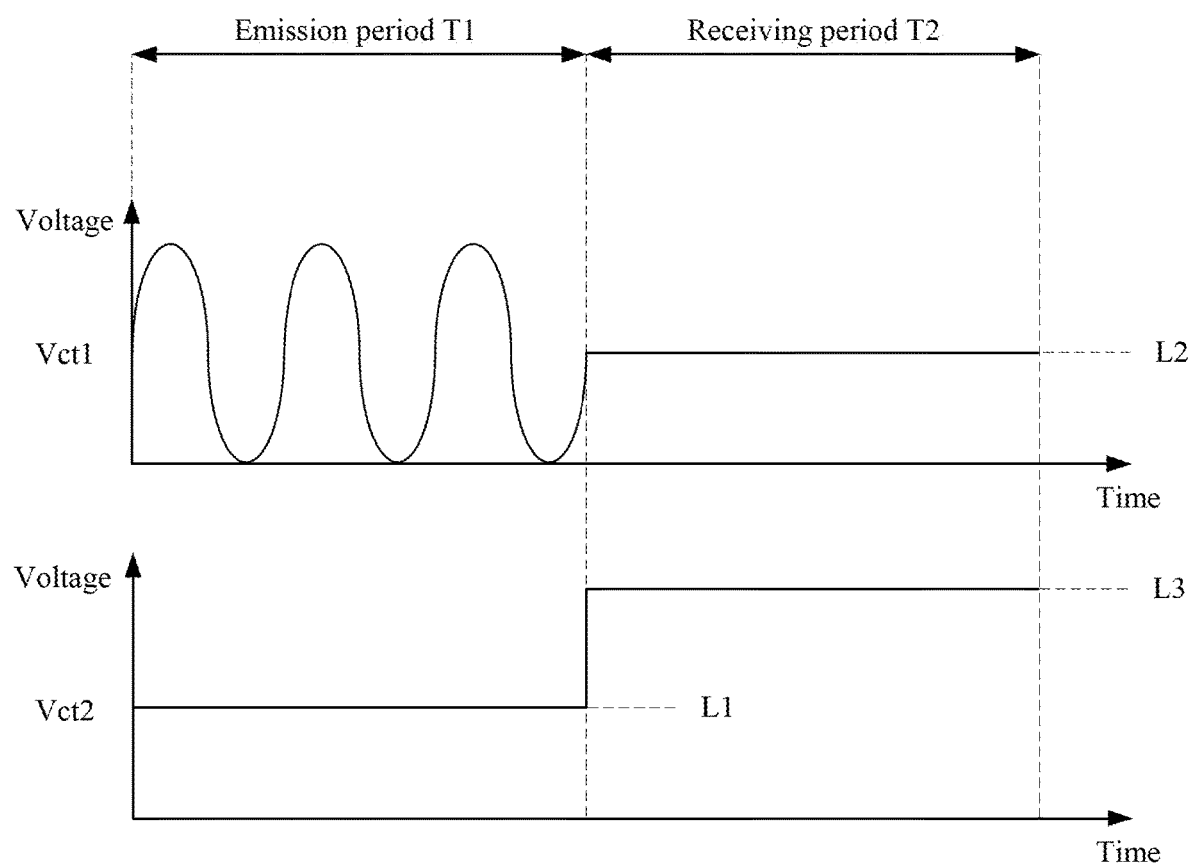
FIG. 2 is a simplified timing diagram for illustrating operations of the ultrasonic wave sensing device of FIG. 1 according to one embodiment of the present disclosure.

FIG. 2 is a simplified timing diagram for illustrating operations of the ultrasonic wave sensing device 100 of FIG. 1 according to one embodiment of the present disclosure. Operations of the ultrasonic wave sensing device 100 will be further described in the following by reference to FIGS. 1 and 2. It is worth mentioning that the operations of the ultrasonic wave sensing device 100 include an emission period T1 and a receiving period T2.

During the emission period T1, the first control signal Vct1 may vibrates periodically (e.g., the first control signal Vct1 may present as a sinusoidal wave). The second control signal Vct2 may maintain at a first voltage level L1 (e.g., a grounding voltage). As a result, the first signal node N1 would have a fixed voltage level corresponding to the first voltage level L1 or the grounding voltage. When the first control signal Vct1 transmits to the ultrasonic wave transducer 120, the ultrasonic wave transducer 120 may generate the ultrasonic wave according to the first control signal Vct1.

In this embodiment, the first voltage level L1 of the second control signal Vct2 is low enough to switch off the reading transistor 110. However, the first control signal Vct1 may transmit to the first signal node N1 through the ultrasonic wave transducer 120, thereby causing the voltage level of the first signal node N1 to vibrate. In this situation, the reading transistor no may erroneously switch from the switched-off status to the conducting status. Therefore, to prevent the processing circuit 101 from acting erroneously, during the emission period T1, the processing circuit 101 would ignore the voltage signal or current signal received from the reading node Nrd.

In some embodiment with no need to concern the power consumption of the ultrasonic wave sensing device 100, during the emission period T1, if the processing circuit 101 ignores the voltage signal or current signal received from the reading node Nrd, no special restrictions are required for the magnitude of the second control signal Vct2.

During the receiving period T2, the first control signal Vct1 may maintain at a second voltage level L2 (e.g., the grounding voltage). The second control signal Vct2 may maintain at a third voltage level L3, wherein the third voltage level L3 is higher than the first voltage level L1. As a result, during the receiving period T2, the voltage level of the first signal node N1 would be corresponding to the third voltage level L3, so as to make the reading transistor 110 conduct and generate the sensing current Isen.

In this situation, if the reflected sound wave, generated by reflecting the ultrasonic wave by an object, is received by the ultrasonic wave transducer 120, the ultrasonic wave transducer 120 may output the sensing signal Vsen to the first signal node N1 according to the reflected sound wave. As a result, the voltage level of the first signal node N1 would be corresponding to the sum of the sensing signal Vsen and second control signal Vct2.

That is, the voltage level of the control node of the reading transistor 110 would be corresponding to the sum of the sensing signal Vsen and second control signal Vct2. The reading transistor 110 may correspondingly determine the magnitude of the sensing current Isen according to the magnitude of the sensing signal Vsen. Once the magnitude of the sensing current Isen varies (e.g., different from a predetermined value), the processing circuit 101 may determine that there is an object nearby the ultrasonic wave sensing device 100.

On the contrary, if the ultrasonic wave transducer 120 does not receive the reflected sound wave, the first signal node N1 would remain at the third voltage level L3, thereby the magnitude of the sensing current Isen would remain constant. In this situation, the processing circuit 101 may determine that there is no object nearby the ultrasonic wave sensing device 100.

In some embodiments, the reading transistor 110 may be realized with P-type transistor. In this situation, during the emission period T1, the second control signal Vct2 may have a higher voltage level to switch off the reading transistor 110. During the receiving period T2, the second control signal Vct2 may have a lower voltage level to conduct the reading transistor 110.

In other embodiments, the ultrasonic wave sensing device 100 comprises multiple amplifiers 140, and the multiple amplifiers 140 couple between the first input node Tx1 and the ultrasonic wave transducer 120 in a series connection.

Figure 3:
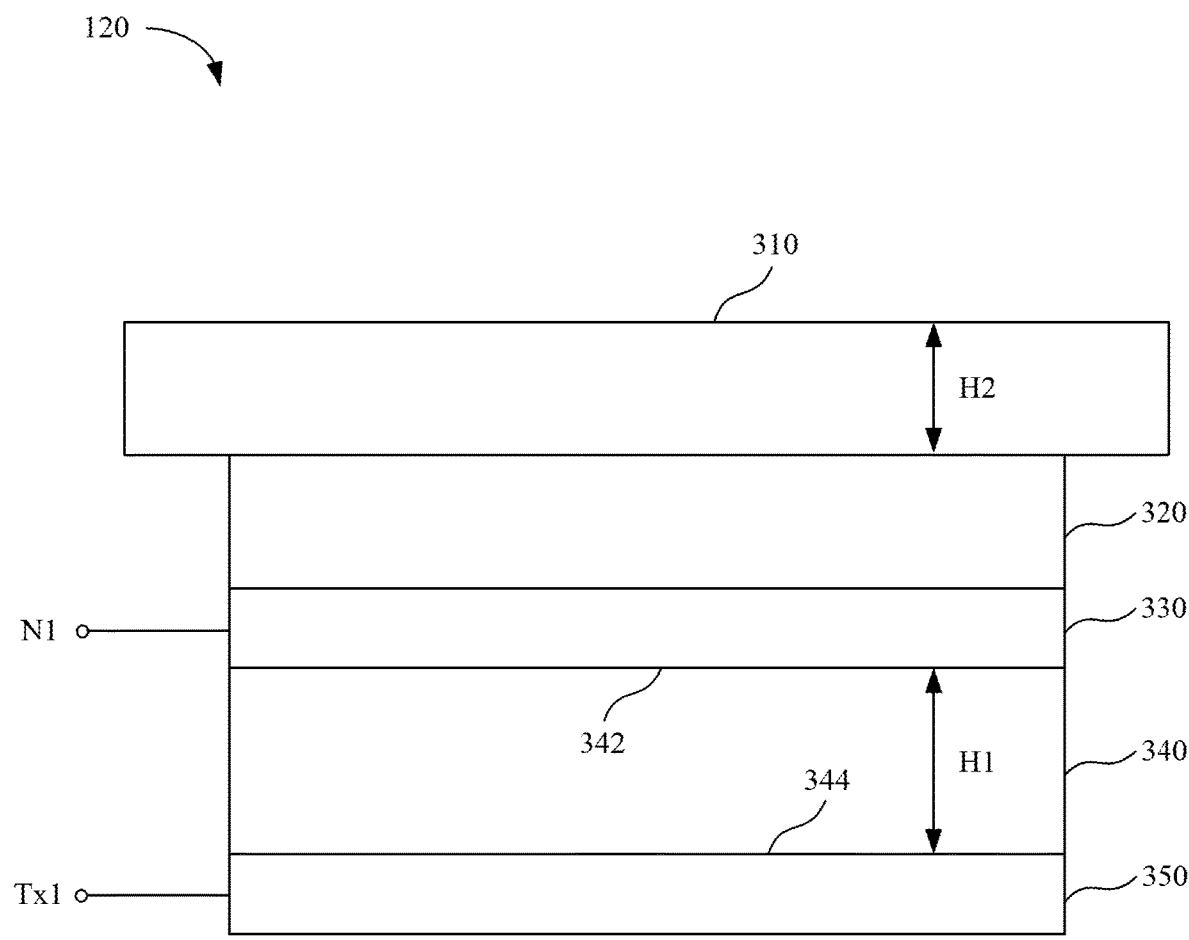
FIG. 3 is a simplified side view of the ultrasonic wave transducer of FIG. 1 according to one embodiment of the present disclosure.

FIG. 3 is a simplified side view of the ultrasonic wave transducer 120 of FIG. 1 according to one embodiment of the present disclosure. In the embodiment of FIG. 3, the ultrasonic wave transducer 120 comprises a surface contact layer 310, an adhesion layer 320, a first conducting layer 330, a signal transceiving layer 340, and a second conducting layer 350. The first conducting layer 330 locates at a first surface 342 of the signal transceiving layer 340, and the second conducting layer 350 locates at a second surface 344 of the signal transceiving layer 340. The adhesion layer 320 locates between the surface contact layer 310 and the first conducting layer 330. That is, the adhesion layer 320 locates between the surface contact layer 310 and signal transceiving layer 340.

Please refer to FIGS. 1 and 3, the signal transceiving layer 340 couples with the first signal node N1 through the first conducting layer 330, and couples with the first input node Tx1 through the second conducting layer 350. Therefore, during the emission period T1, the signal transceiving layer 340 may generate the ultrasonic wave according to the first control signal Vct1 and the second control signal Vct2. In addition, during the receiving period T2, the signal transceiving layer 340 may generate the sensing signal Vsen according to the received reflected sound wave, and output the sensing signal Vsen to the first signal node N1.

That is, the signal transceiving layer 340 can realize the ultrasonic wave emission and receiving function by a single layer structure. Because of the signal layer structure of the transceiving layer 340, when sound wave (e.g., the ultrasonic wave) transmits in the signal transceiving layer 340, the sound wave may have a fixed sound velocity (e.g., first sound velocity). In addition, when the sound wave transmits in the surface contact layer 310, the sound wave may have another fixed sound velocity (e.g., second sound velocity).

It is worth mentioning that the thickness of the signal transceiving layer 340 is first thickness H1, and the thickness of the surface contact layer 310 is second thickness H2. The ratio of the first thickness H1 to the second thickness H2 is the same as or approximates the ratio of the first sound velocity to the second sound velocity.

In practice, the surface contact layer 310 may be realized with any suitable metal material, and the adhesion layer 320 may be realized with ultrasound gel. The first conducting layer 330 and the second conducting layer 350 may be realized with silver conducting paste. The signal transceiving layer 340 may be realized with any suitable piezoelectric material such as lead zirconium titanate (PZT) or polyvinylidene difluoride (PVDF).

Figure 4:
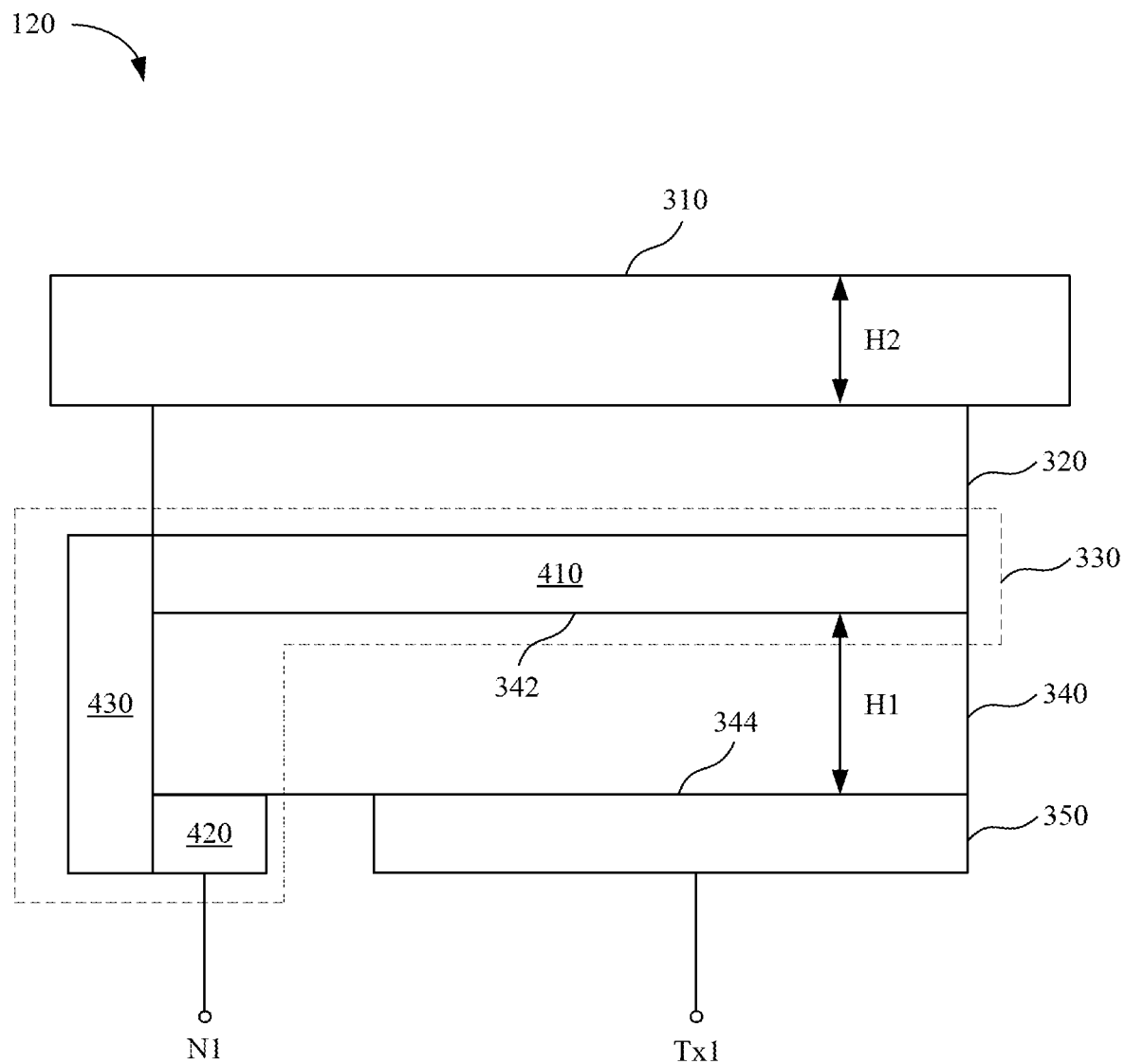
FIG. 4 is a simplified side view of the ultrasonic wave transducer of FIG. 1 according to another embodiment of the present disclosure.

FIG. 4 is a simplified side view of the ultrasonic wave transducer of FIG. 1 according to another embodiment of the present disclosure. The ultrasonic wave transducer 120 of FIG. 4 is similar to the ultrasonic wave transducer 120 of FIG. 3, the difference is that the first conducting layer 330 of the ultrasonic wave transducer 120 of FIG. 4 comprises a first portion 410, a second portion 420, and a third portion 430. The first portion 410 locates between the adhesion layer 320 and the first surface 342 of the signal transceiving layer 340. The second portion 420 locates at the second surface 344 of the signal transceiving layer 340. The third portion 430 couples with the first portion 410 and the second portion 420.

That is, the first portion 410 and the third portion 430 are approximately perpendicular to each other, so as to form an L-shaped structure. The second portion 420 and the third portion 430 are also approximately perpendicular to each other, so as to form an L-shaped structure.

In one embodiment, the first portion 410, second portion 420, and third portion 430 of the first conducting layer 330 may be realized with continuously coated silver conducting past, or be realized with any other integrally formed conducted material. In another embodiment, the first portion 410, second portion 420, and third portion 430 of the first conducting layer 330 may be realized with multiple conducted materials coupling with each other.

Since the first conducting layer 330 extends to the second surface 344 of the signal transceiving layer 340, in this embodiment, all signal input nodes of the ultrasonic wave transducer 120 locate at a same surface. As a result, the difficulty of assembling the whole circuit can be reduced. For example, in the situation that the third portion 430 of the first conducting layer 330 couples with the first signal node N1 and the second conducting layer 350 couples with the first input node Tx1, the signal input nodes of the ultrasonic wave transducer 120 are all locates at the second surface 344 of the signal transceiving layer 340.

As can be appreciated from the foregoing descriptions, comparing to the traditional ultrasonic wave sensing system, the ultrasonic wave sensing device 100 provides the signal transceiving layer 340 to simultaneously realize the ultrasonic wave emission and receiving function. That is, the ultrasonic wave sensing device 100 has no need to contain an individual ultrasonic wave emission layer and an individual ultrasonic wave receiving layer. Therefore, the ultrasonic wave sensing device 100 has advantages such as simple structure and easily to be assembled.

Certain terms are used throughout the description and the claims to refer to particular components. One skilled in the art appreciates that a component may be referred to as different names. This disclosure does not intend to distinguish between components that differ in name but not in function. In the description and in the claims, the term "comprise" is used in an open-ended fashion, and thus should be interpreted to mean "include, but not limited to." The term "couple" is intended to compass any indirect or direct connection. Accordingly, if this disclosure mentioned that a first device is coupled with a second device, it means that the first device may be directly or indirectly connected to the second device through electrical connections, wireless communications, optical communications, or other signal connections with/without other intermediate devices or connection means.

The term "signal" used throughout the description and the claims may be expressed in the format of a current or a voltage in implementations.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An ultrasonic wave sensing device comprising:
   a reading transistor, comprising a first node, a second node, and a control node, wherein the first node of the reading transistor is configured to receive a reference voltage, the second node of the reading transistor is configured for coupling with a reading node, and the control node of the reading transistor is coupled with a first signal node;
   an ultrasonic wave transducer, coupled between the first signal node and a first input node, and configured to receive a first control signal from the first input node; and
   an input circuit, coupled between the first signal node and a second input node, and configured to receive a second control signal from the second input node,
   wherein the ultrasonic wave transducer is further configured to generate an ultrasonic wave according to the first control signal and the second control signal,
   wherein when the first control signal vibrates periodically and the ultrasonic wave transducer generates the ultrasonic wave, the input circuit provides the second control signal having a first voltage level to the first signal node to switch off the reading transistor,
   when the first control signal has a second voltage level and the ultrasonic wave transducer outputs a sensing signal to the first signal node according to a reflected sound wave corresponding to the ultrasonic wave, the input circuit provides the second control signal having a third voltage level to the first signal node to conduct the reading transistor, and the first voltage level is different from the third voltage level.

2. The ultrasonic wave sensing device of claim 1, wherein the reading transistor determines magnitude of a sensing current according to the sensing signal, and the sensing current transmits to the reading node through the reading transistor.

3. The ultrasonic wave sensing device of claim 1, wherein the input circuit comprises:
   a resistor; and
   a Zener diode, comprising an anode node and a cathode node;

wherein the resistor is coupled between the first signal node and the second input node, the cathode node of the Zener diode is coupled with the first signal node, and the anode node of the Zener diode is coupled with the second input node.

4. The ultrasonic wave sensing device of claim 1, wherein the ultrasonic wave transducer comprises:
   a surface contact layer;
   a signal transceiving layer, coupled between the first signal node and first input node, and configured to generate the ultrasonic wave according to the first control signal and the second control signal; and
   an adhesion layer, located between the surface contact layer and the signal transceiving layer.

5. The ultrasonic wave sensing device of claim 4, wherein the ultrasonic wave transducer further comprises:
   a first conducting layer, located between the adhesion layer and a first surface of the signal transceiving layer, and coupled with the first signal node; and
   a second conducting layer, located at a second surface of the signal transceiving layer, and coupled with the first input node.

6. The ultrasonic wave sensing device of claim 4, wherein the ultrasonic wave transducer further comprises:
   a first conducting layer, comprising:
      a first portion, located between the adhesion layer and a first surface of the signal transceiving layer;
      a second portion, located at a second surface of the signal transceiving layer; and
      a third portion, coupled with the first portion and the second portion; and
   a second conducting layer, located at the second surface of the signal transceiving layer, and coupled with the first input node.

7. The ultrasonic wave sensing device of claim 4, wherein when the ultrasonic wave transmits in the signal transceiving layer, a transmitting speed of the ultrasonic wave maintains at a first sound velocity.

8. The ultrasonic wave sensing device of claim 7, wherein the signal transceiving layer has a first thickness and the surface contact layer has a second thickness,
   wherein when the ultrasonic wave transmits in the surface contact layer, the transmitting speed of the ultrasonic wave maintains at a second sound velocity, and a ratio of the first thickness to the second thickness equals to a ratio of the first sound velocity to the second sound velocity.

* * * * *